(12) United States Patent
Lim et al.

(10) Patent No.: US 7,402,076 B1
(45) Date of Patent: Jul. 22, 2008

(54) RETAINING MECHANISM FOR AN IMPLANTABLE MEDICAL DEVICE CONNECTOR ASSEMBLY

(75) Inventors: Wisit Lim, Palmdale, CA (US); Narendra Nayak, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 11/553,318

(22) Filed: Oct. 26, 2006

(51) Int. Cl.
*H01R 13/58* (2006.01)
(52) U.S. Cl. ..................................... 439/462
(58) Field of Classification Search ................. 439/462, 439/909, 811, 668; 607/37, 38, 122; 128/419 P
See application file for complete search history.

(56) References Cited

U.S. PATENT DOCUMENTS

| | | | | |
|---|---|---|---|---|
| 4,316,471 A | * | 2/1982 | Shipko et al. | 607/37 |
| 4,461,194 A | * | 7/1984 | Moore | 81/436 |
| 5,542,794 A | * | 8/1996 | Smith et al. | 407/35 |
| 6,227,782 B1 | * | 5/2001 | Bowling et al. | 411/114 |
| 6,428,368 B1 | * | 8/2002 | Hawkins et al. | 439/271 |
| 6,984,145 B1 | | 1/2006 | Lim | |
| 7,029,293 B2 | * | 4/2006 | Shapson et al. | 439/97 |
| 7,033,231 B2 | * | 4/2006 | Lu | 439/812 |
| 7,231,253 B2 | * | 6/2007 | Tidemand et al. | 607/37 |

* cited by examiner

*Primary Examiner*—Alexander Gilman (57) ABSTRACT

A connector assembly for an implantable medical device includes a support body having a receptacle connector extending therefrom. The receptacle connector is configured to receive a lead therein, and the support body has a fastener bore. The connector assembly also includes clamp having a clamp fastener bore, wherein the clamp is movable with respect to the support body to receive the lead between the clamp and the support body. A threaded fastener is received in the fastener bore and the clamp fastener bore for securing the clamp to the support body. The threaded fastener has first and second sets of threads for engaging first and second threaded portions, respectively, wherein the first and second threaded portions are included in at least one of the fastener bore and the clamp fastener bore. The first and second sets of threads have different thread types.

18 Claims, 7 Drawing Sheets

RETAINING MECHANISM FOR AN IMPLANTABLE MEDICAL DEVICE CONNECTOR ASSEMBLY

FIELD OF THE INVENTION

Embodiments relate generally to electrical connector assemblies that are provided as part of implantable medical devices (IMD's), and more particularly, to fastening mechanisms that are provided as part of an IMD connector assembly for securely locking an implantable lead within the connector assembly.

BACKGROUND OF THE INVENTION

IMD's are used today in a variety of applications. In general IMD's include a connector assembly that has one or more electrical receptacles each adapted to receive a corresponding lead and to connect the lead to electronic circuits within the IMD. By way of example, an IMD may be a cardiac pacemaker, or other implantable stimulation device, such as a cardioverter or a defibrillator. By way of further example, an IMD may also be an appetite suppression device, a nervous or muscle stimulation device, a pain reduction device, a medicine delivery device, and the like. The IMD includes a hermetically sealed housing or casing (sometimes also referred to as a "can") to isolate the electronic circuits contained within the device from the body environment. Such devices require that electrical signals be reliably passed between the sealed circuitry and external connectors without compromising the isolation of the electronics. Depending on the configuration of the IMD there may be multiple electrical paths that extend between the device and the external connectors to deliver, for example, multi-chamber or multi-site stimulation and shock therapy, and to receive sensed cardiac signals. The electrical paths must be electrically and mechanically integrated with the device to provide a safe, long-term connector assembly that does not compromise the hermetic package.

Typically, the housing is provided with a feedthrough assembly that electrically couples the electronic circuits contained within the device housing to the connector assembly. The feedthrough assembly extends through the wall of the sealed casing to the connector assembly and couples the electronic circuits within the casing to lead-receiving receptacles within the connector assembly. Each lead has one or more electrical terminals on a proximal end thereof, typically in the form of a pin terminal and one or more conductive ring terminals. The pin may be electrically coupled to a distal tip electrode. When the proximal end of the lead is inserted into the lead receptacle of a connector assembly, contacts within the receptacle engage corresponding pin terminals on the lead to couple the lead to the electronic circuits within the IMD via the feedthrough assembly. A dependable electrical connection is made and retained between the lead terminals and the corresponding connector assembly contacts. At the same time, the connector assembly must be capable of releasing the lead from the lead receptacle during explanation or other subsequent procedures, and must also tightly seal against entry of body fluids.

Conventional connector assemblies electrically and mechanically connect the proximal end of the lead within a receptacle of the connector assembly by means of a variety of captive fastening screw/collet arrangements and setscrews. In prior art connector assemblies in which the lead is fixed within the lead receptacle using a setscrew, the setscrew is often threaded into an electrical connector block within the connector assembly. When the screw is advanced, it comes into contact with an associated terminal on the proximal end of the lead, mechanically and electrically coupling the lead and the connector assembly. However, the proximal end of a lead is sometimes damaged by an over-tightened setscrew. Also, the setscrews may strip out of the threaded connector block. To address such problems, large setscrews of a certain physical size have been employed. The result is that the setscrew protrudes from the side of the connector assembly, which becomes more noticeable as the physical size of the IMD and connector assembly is reduced.

A further problem of prior art setscrew type connector assemblies arises from the need to isolate the setscrew and the setscrew block from body fluids. One solution has been to use a silicone seal called a septum. The septum forms an insulation barrier between the setscrew and body fluids. However, the septum must permit a wrench to pass through the septum so that the setscrew can be tightened. Frequently, the septum is damaged by the wrench resulting in a loss of the isolation barrier.

Accordingly, it would be desirable to provide a retaining mechanism for a connector assembly for securing and locking the proximal end of a lead to an IMD which will prevent complete retraction or removal of the retaining mechanism from the connector assembly.

SUMMARY

In one aspect, a connector assembly for an implantable medical device is provided, wherein the connector assembly includes a support body having a receptacle connector extending therefrom. The receptacle connector is configured to receive a lead therein, and the support body has a fastener bore. The connector assembly also includes clamp having a clamp fastener bore, wherein the clamp is movable with respect to the support body to receive the lead between the clamp and the support body. A threaded fastener is received in the fastener bore and the clamp fastener bore for securing the clamp to the support body. The threaded fastener has first and second sets of threads for engaging first and second threaded portions, respectively, wherein the first and second threaded portions are included in at least one of the fastener bore and the clamp fastener bore. The first and second sets of threads have different thread types.

In another aspect, an implantable medical device is provided including an implantable lead, a sealed casing having electronic circuitry therein, and a header assembly for interconnecting the electronic circuitry with the implantable lead. The header assembly includes a support body having a receptacle connector extending therefrom, wherein the receptacle connector receives the implantable lead therein and is electrically coupled to the electronic circuitry. The support body has a fastener bore. The header assembly also includes a clamp having a clamp fastener bore, wherein the clamp is movable with respect to the support body to receive the lead between the clamp and the support body. A threaded fastener is received in the fastener bore and the clamp fastener bore for securing the clamp to the support body. The threaded fastener has first and second sets of threads for engaging first and second threaded portions, respectively, wherein the first and second threaded portions are included in at least one of the fastener bore and the clamp fastener bore. The first and second sets of threads have different thread types.

In a further aspect, a method of connecting a lead to a connector assembly of an implantable device is provided including providing a support body and a clamp movable with respect to the support body, wherein the support body includes a fastener bore and the clamp includes a clamp fastener bore, providing a first threaded portion and a second threaded portion, wherein the first and second threaded portions are included on at least one of the support body and the clamp, and providing a fastener including a first set of threads and a second set of threads, wherein the threads of the first set of threads are threaded in a first direction and the threads of the second set of threads are threaded in a second direction. The method also includes threadably coupling the second set of threads to the second threaded portion by rotating the fastener in a first direction such that the clamp is loosely coupled to the support body, positioning the lead between the clamp and the support body, and threadably coupling the first set of threads to first threaded portion by rotating the fastener in a second direction that is opposite the first direction such that the clamp is securely coupled to the support body and such that the lead is securely retained between the clamp and the support body.

DETAILED DESCRIPTION

Figure 1:
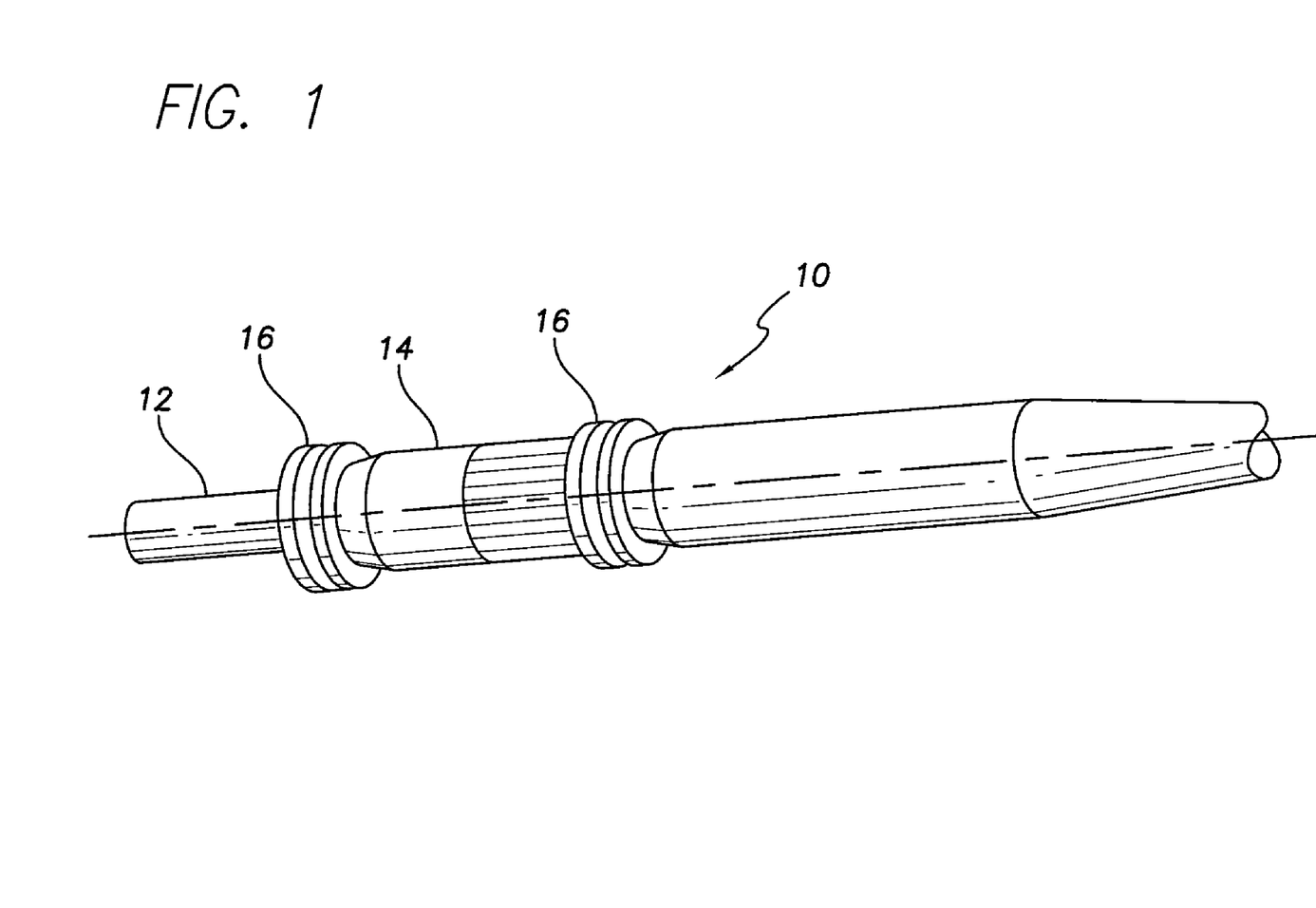
FIG. 1 is a perspective view of a proximal end portion of a conventional bipolar lead.

FIG. 1 shows a proximal end portion 10 of a conventional transvenous, bipolar pacing lead. The diameter of such a lead may be made sufficiently small to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads having proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

Bipolar coaxial leads typically include a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10, shown in FIG. 1, conforms to the IS-1 standard, comprising a pair of coaxial spaced-apart terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead may each be engaged by a conductive garter spring contact or other resilient electrical contact element carried by a connector assembly in a manner such as that described in accordance with the connector assembly described in U.S. Pat. No. 6,984,145, issued Jan. 10, 2006, the complete subject matter of which has been incorporated by reference in its entirety. The proximal lead end portion 10 further includes spaced-apart pairs of seal rings 16 for preventing body fluids from reaching the electrical contacts. With the proximal end portion 10 of the lead inserted in a lead receptacle of a connector assembly, the tip and ring terminals 12 and 14 are electrically coupled via the contacts and a feedthrough to the electronic circuits within the IMD.

Figure 2:
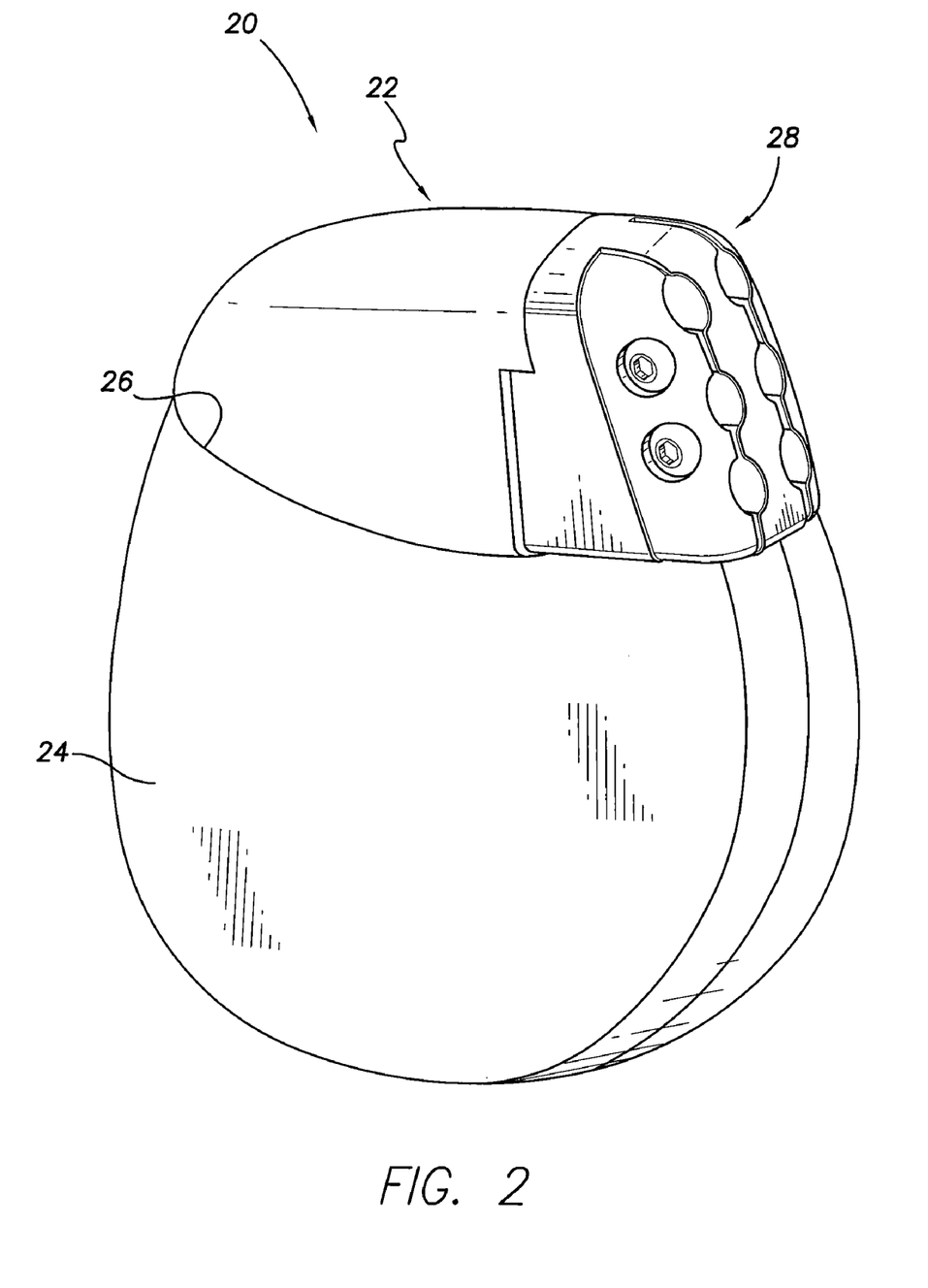
FIG. 2 is a perspective side view of an implantable medical device (IMD) including a header assembly formed in accordance with an exemplary embodiment.

FIG. 2 is a perspective side view of an IMD 20 including a header assembly 22 formed in accordance with an exemplary embodiment. The IMD 20 includes a hermetically sealed can or casing 24 enclosing the electronic components. The header assembly 22 is mounted along a top edge 26 of the IMD 20. The header assembly 22 includes a connector assembly 28. Although the following embodiments are described principally in the context of pacemaker/defibrillator unit capable of sensing and/or pacing pulse delivery, the invention may be applied to other IMD structures. As further examples, embodiments may be implemented in devices that suppress an individual's appetite, reduce or offset pain associated with chronic conditions and control motor skills for handicap individuals.

Figure 3:
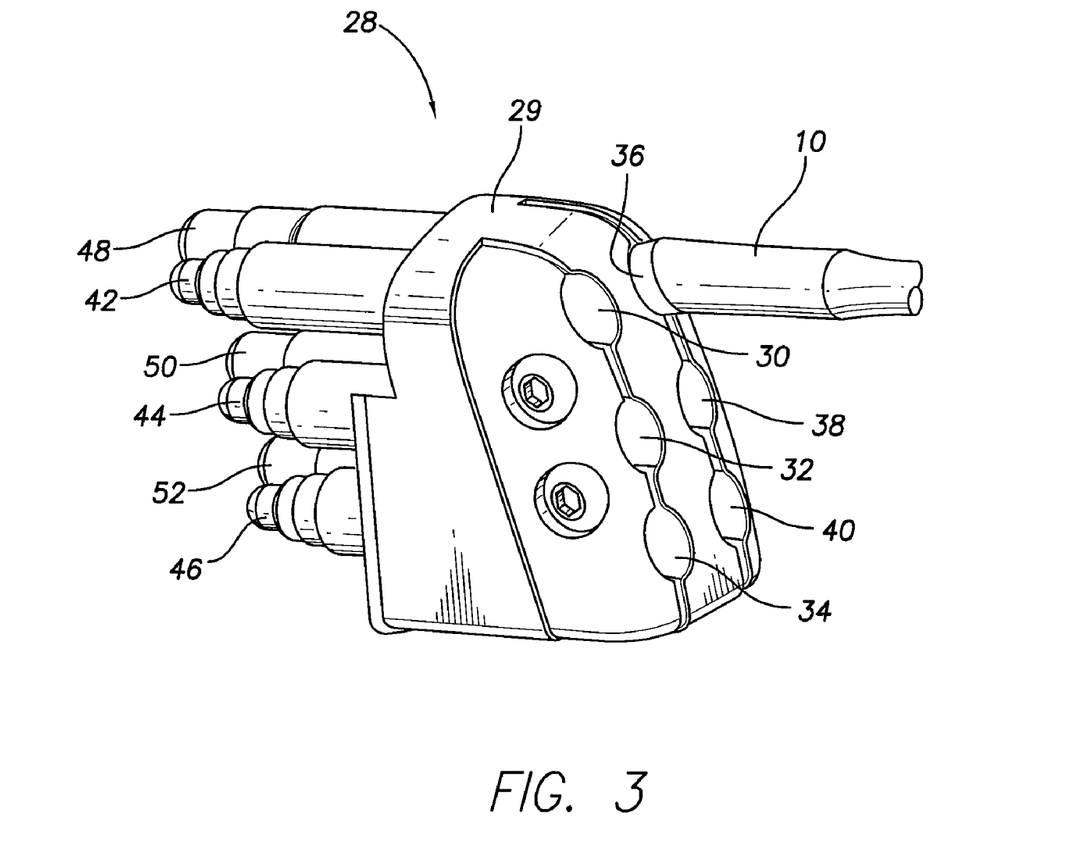
FIG. 3 is a perspective side view of a connector assembly removed from the header assembly of the IMD shown in FIG. 2.

FIG. 3 is a perspective side view of the connector assembly 28 removed from the header assembly 22. The connector assembly 28 is utilized to receive multiple leads and facilitate interconnection of the proximal end portion 10 of the lead with the electrical components of the IMD 20 (shown in FIG. 2). In the illustrated embodiment, the connector assembly 28 includes a support body 29 configured to support a plurality of receptacle connectors 42, 44, 46, 48, 50 and 52. Each of the receptacle connectors 42, 44, 46, 48, 50 and 52 have a corresponding receptacle 30, 32, 34, 36, 38 and 40 extending longitudinally through the connector assembly 28. In alternative embodiments, more or less receptacle connectors and corresponding receptacles may be provided depending on the type of IMD 20.

The receptacles 30, 32, 34, 36, 38 and 40 are open at a mating end of the connector assembly 28 and extend into the receptacle connectors 42, 44, 46, 48, 50 and 52. The receptacles 30, 32, 34, 36, 38 and 40 receive the leads and provide access for the leads to the receptacle connectors 42, 44, 46, 48, 50 and 52. FIG. 3 shows the proximal end portion 10 of a lead inserted in the lead receptacle 36 and interconnected with the receptacle connector 48. The receptacle connectors 42, 44, 46, 48, 50 and 52 electrically connect the leads received within the corresponding receptacles 30, 32, 34, 36, 38 and 40 with the electronic components of the IMD 20. The electrical interconnection of the leads and the electrical components of the IMD 20 may be accomplished in a manner such as that described in accordance with the connector assembly described in U.S. Pat. No. 6,984,145.

Figure 4:
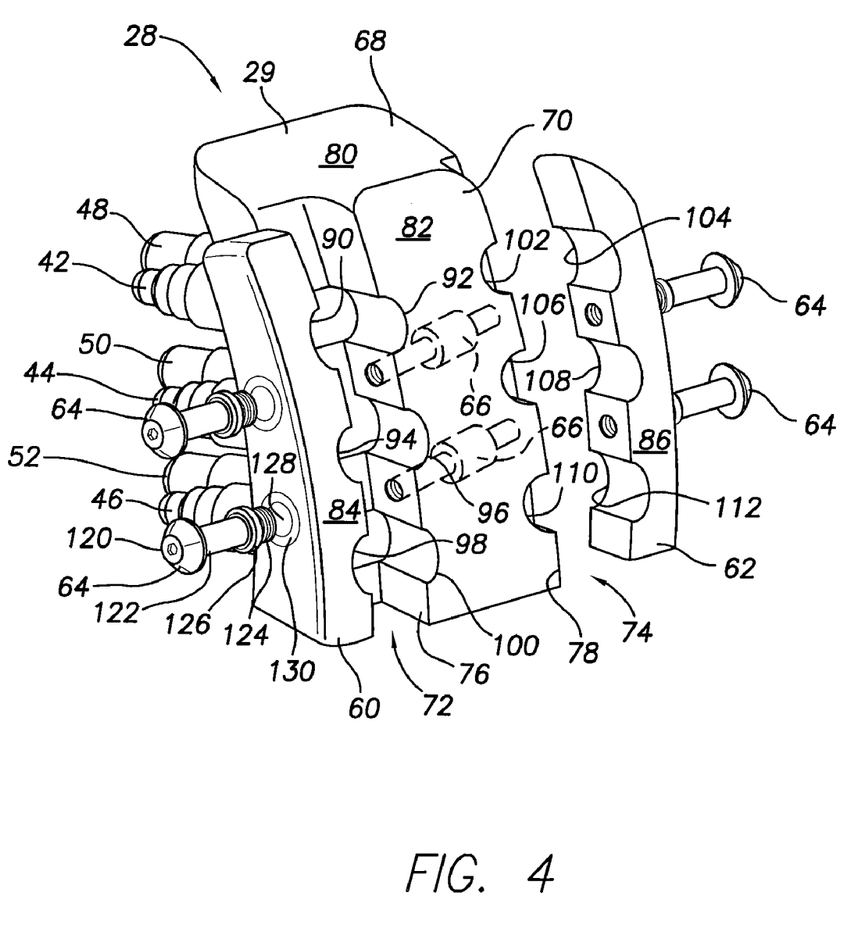
FIG. 4 is an exploded side view of the connector assembly shown in FIG. 3 and illustrating fasteners and a threaded inserts formed in accordance with an exemplary embodiment.

FIG. 4 is an exploded side view of the connector assembly 28, first and second opposed side clamps 60 and 62, respectively, a plurality of fasteners 64 and multiple threaded inserts 66. The side clamps 60, 62 are separately provided from the support body 29 and are removable from the support body 29. Alternatively, the side clamps 60, 62 may be coupled to the support body 29 and movable with respect to the support body 29, such as by a hinge connection. In one alternative embodiment, a portion of the support body 29 may be movable with respect to the side clamps 60, 62 such as by a hinge connection. The fasteners 64 may be threadably coupled to the threaded inserts 66 to secure the side clamps 60, 62 to the support body 29. For example, during tightening of the fasteners 64, the side clamps 60, 62 and/or the support body 29 are moved relatively closer to one another. Optionally, when the side-clamps 60, 62 are secured to the support body, the side clamps 60, 62 and the support body 29 may define a front portion of the receptacles 30, 32, 34, 36, 38 and 40 (shown in FIG. 3) that receive the leads. The leads may be placed in the receptacles 30, 32, 34, 36, 38 and 40 prior to tightening the fasteners 64 to secure the side clamps 60, 62 to the support body 29 to lock the leads in place. Alternatively, the leads may be secured within the receptacles 30, 32, 34, 36, 38 and 40 by a structure other than the side clamps 60, 62 and the support body 29, in which case, the side clamps 60, 62 and the support body 29 operate to support a portion of the lead at a front end of the receptacles 30, 32, 34, 36, 38 and 40.

The support body 29 includes a rear portion 68 and a front portion 70, narrower than the rear portion 68. The lead connectors 42, 44, 46, 48, 50 and 52 extend rearward from the rear portion 68. The front portion 70 defines a mating end of the connector assembly 28 for mating with the leads. Alternatively, the leads may be mated to other portions of the connector assembly 28 other than the front portion 70, such as a side or a top of the connector assembly 28. Optionally, the support body 29 and side clamps 60, 62 may be molded of a material such as polysulfone or other biocompatible thermoplastics.

Oriented on opposite sides of the front portion 70 are first and second side recesses 72 and 74, respectively. The side recesses 72, 74 are provided to receive the side clamps 60, 62, respectively. The side recesses 72, 74 include opposed, parallel side surfaces 76 and 78, respectively. The rear portion 68, the front portion 70 and the side clamps 60, 62 have curved outer surfaces 80, 82, 84 and 86, respectively, that form a substantially continuous, smooth, outer connector assembly surface when the side clamps 60, 62 are assembled and secured to the support body 29 using the fasteners 64, as seen, for example, in FIG. 3.

Each of the right side receptacles 30, 32 and 34 are defined by a portion of the side clamp 60 and a portion of the support body 29. As illustrated in FIG. 4, the side clamp 60 includes grooves or channels 90, 94 and 98 defining a portion of the receptacles 30, 32 and 34, respectively. Optionally, the channels 90, 94 and 98 may define a portion of the front part of the receptacles 30, 32 and 34. Similarly, the side surface 76 of the front portion 70 of the support body 29 includes grooves or channels 92, 96 and 100 defining another portion of the receptacles 30, 32 and 34, respectively. The channels 92, 96 and 100 may define a portion of the front part of the receptacles 30, 32 and 34. In the illustrated embodiment, each of the receptacles 30, 32 and 34 are bisected and defined, at least in part, by the side clamp 60, and, at least in part, by the support body 29. The channels 90 and 92 cooperate to define the receptacle 30; the channels 94 and 96 cooperate to define the receptacle 32; and the channels 98 and 100 cooperate to define the receptacle 34. Optionally, the channels 90, 92, 94, 96, 98 and 100 may be symmetrical about a vertical interface plane thus forming equal portions of the front part of the respective receptacle 30, 32, 34, or alternatively, the channels 90, 92, 94, 96, 98 and 100 may form unequal portions of the receptacles 30, 32, 34. In alternative embodiments, the channels may be provided on different surfaces of the side clamp 60 and/or the support body 29.

In similar fashion, each of the left side receptacles 36, 38 and 40 are defined by a portion of the side clamp 62 and a portion of the support body 29. As illustrated in FIG. 4, the side clamp 62 includes grooves or channels 104, 108, and 112 defining a portion of the receptacles 36, 38 and 40, respectively. Optionally, the channels 104, 108, and 112 may define a portion of the front part of the receptacles 36, 38 and 40. Similarly, the side surface 78 of the front portion 70 of the support body 29 includes grooves or channels 102, 106 and 110 defining another portion of the receptacles 36, 38 and 40, respectively. In the illustrated embodiment, each of the receptacles 36, 38 and 40 are bisected and defined, at least in part, by the side clamp 62, and, at least in part, by the support body 29. The channels 102 and 104 cooperate to define the receptacle 36; the channels 106 and 108 cooperate to define the receptacle 38; and the channels 110 and 112 cooperate to define the receptacle 40. Optionally, the channels 102, 104, 106, 108, 110 and 112 may be symmetrical about a vertical interface plane thus forming equal portions of the front part of the respective receptacle 36, 38 and 40, or alternatively, the channels 102, 104, 106, 108, 110 and 112 may form unequal portions of the receptacles 36, 38 and 40. In alternative embodiments, the channels may be provided on different surfaces of the side clamp 62 and/or the support body 29.

As illustrated in FIG. 4, the narrow, front portion 70 of the support body 29 includes the threaded inserts 66 (shown in phantom in FIG. 4). Alternatively, the side clamps 60, 62 may include the threaded inserts 66 therein such that the fasteners 64 extend through the support body 29 and couple to the insert 66 in the side clamps 60, 62. Alternatively, each of the support body 29 and the side clamps 60, 62 may include threaded inserts 66 for engaging the fasteners 64. Optionally, the threaded inserts 66 may be formed of metal, and may be co-molded with the support body 29 so as to be securely affixed thereto. Alternatively, the threaded inserts 66 and the support body 29 may be separately manufactured and then coupled together. In other alternative embodiments, a separate threaded insert is not provided, but rather, the support body 29 may include a threaded bore that is formed therein during forming of the support body 29, or that is manufactured or milled in the support body 29 after forming of the support body 29. Optionally, the threaded inserts 66 and/or the support body 29 may form part of a retro-fit kit, such that existing connector assemblies may be retro-fit to accept the threaded inserts 66 for receiving the fasteners 64. In the illustrated embodiment, the threaded inserts 66 are exposed at the side surfaces 76 and 78 to the side clamps 60, 62 and the fasteners 64. The threaded inserts 66 include an opening for receiving the fasteners 64 therein, and the opening defines a fastener bore. The fastener bore is threaded for threadable engagement with the threaded fasteners 64. Optionally, each threaded insert 66 is open at both ends thereof and extends completely between the side surfaces 76 and 78 such that the threaded insert 66 is engaged by two fasteners 64, one at each end. Alternatively, each threaded insert 66 is only open at one end and engages a single fastener 64.

The threaded fasteners 64 each include a head 120 and a shaft 122 extending from the head 120. Optionally, the threaded fasteners 64 may constitute compound screws. Each shaft 122 includes a first set of threads 124 for engaging a first threaded portion of the threaded insert 66 and a second set of threads 126 for engaging a second threaded portion of the threaded insert 66. The engagement between the threaded portions of the threaded inserts 66 and the threads of the fasteners 64 will be described in further detail below. The shafts 122 are sized to fit through fastener bores 128 that extend completely through the side clamps 60, 62. Optionally, the side clamps 60, 62 may include counterbores 130 that are sized to receive the heads 120 such that the heads 120 are recessed with respect to the outer surfaces of the side clamps 60, 62, as seen, for example, in FIG. 3.

During assembly, the shafts 122 of the threaded fasteners 64 are passed through the fastener bores 128 and engage the threaded inserts 66, such that the side clamps 60, 62 and the fasteners 64 are loosely preassembled. The leads may then be loosely placed in the receptacles 30, 32, 34, 36, 38 and 40. As the fasteners 64 are tightened to the threaded inserts 66, the heads 120 of the threaded fasteners 64 engage the side clamps 60, 62 and press the side clamps 60, 62 to the side surfaces 76, 78, respectively, of the front portion 70 of the support body 29. When the leads are positioned within the channels 90, 92, 94, 96, 98 and 100, the leads are locked into place within the receptacles 30, 32 and 34 by the side clamp 60. As such, the fasteners 64 and the threaded inserts 66 define retaining or locking mechanisms for the connector assembly 28 of the IMD 20. An exemplary operation of the locking mechanism will now be described in more detail with reference to FIGS. 5-9.

Figure 5:
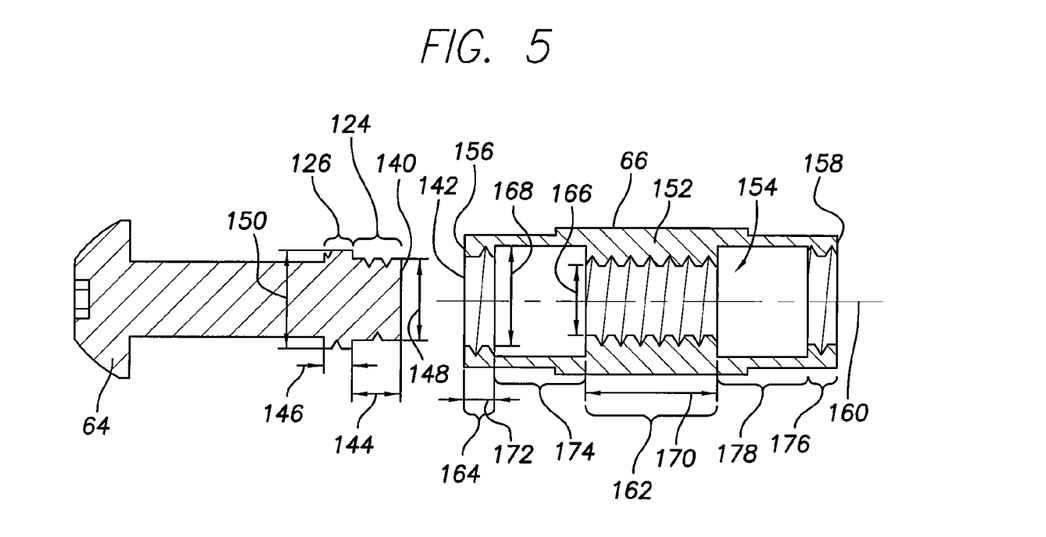
FIG. 5 illustrates an exemplary position of one of the fasteners with respect to one of the threaded inserts, both shown in FIG. 4, prior to mating of the fastener with the threaded insert.

FIG. 5 illustrates an exemplary position of one of the fasteners 64 with respect to one of the threaded inserts 66 prior to mating of the fastener 64 with the threaded insert 66 (e.g. a pre-assembly or pre-mating position). During pre-assembly, the fastener 64 may be pre-loaded into the fastener bore 128 (shown in FIG. 4) of the side clamp 60 (shown in FIG. 4), and an end 140 of the threaded fastener 64 is aligned with an opening 142 of the threaded insert 66. As illustrated in FIG. 5, the first set of threads 124 are oriented at the end 140 of the fastener 64 and extend along a length 144 to the second set of threads 126. The second set of threads 126 extend along a length 146.

As illustrated in FIG. 5, the first and second sets of threads 124, 126 have different thread types. The thread types are characterized by factors such as the thread direction (e.g. right handed thread, left-handed thread), the major diameter of the threads, the pitch of the threads, the thread angle, the depth of the thread, and the like. Optionally, the first set of threads 124 may have a first diameter 148 and the second set of threads 126 may have a second, larger diameter 150. As will become evident from the description below, the diameters 148, 150 of the sets of threads 124, 126 allow interaction with particular threaded portions of the threaded insert 66 and restrict interaction with certain other threaded portions of the threaded insert 66. Optionally, the first set of threads 124 may have external threads that are arranged in a first direction (e.g. right-handed threads) and the second set of threads 126 may have external threads that are arranged in a second, opposite direction (e.g. left-handed threads). Accordingly, clockwise rotation of the fastener 64 will cause the first set of threads 124 to advance when engaging the threaded insert 66, but will cause the second set of threads 126 to retract when engaging the threaded insert 66. Likewise, counter-clockwise rotation of the fastener 64 will cause the first set of threads 124 to retract when engaging the threaded insert 66, but will cause the second set of threads 126 to advance when engaging the threaded insert 66. In alternative embodiments, the sets of threads 124, 126 may have threads that have different pitches in the same direction, the sets of threads 124, 126 may have threads that have a different thread angle, the sets of threads 124, 126 may have threads that have different depths of threads, and the like to allow interaction with particular threaded portions of the threaded insert 66 and restrict interaction with certain other threaded portions of the threaded insert 66.

The threaded insert 66 includes a body or housing 152 having a through-bore 154 extending from a first end 156 to a second end 158 along a longitudinal axis 160. The insert 66 includes a first threaded portion 162 and a second threaded portion 164 configured to interact with the first set of threads 124 and the second set of threads 126, respectively, of the fastener 64. The first and second threaded portions 162, 164 have different thread types. The thread types are characterized by factors such as the thread direction (e.g. right handed thread, left-handed thread), the major diameter of the threads, the pitch of the threads, the thread angle, the depth of the thread, and the like. Optionally, the first threaded portion 162 may have an opening with a first diameter 166 and the second threaded portion may have an opening with a second, larger diameter 168. As will become evident from the description below, the diameters 166, 168 of the threaded portions 162, 164 allow interaction with particular sets of threads of the threaded fastener 64 and restrict interaction with certain other sets of threads of the threaded fastener 64. Optionally, the first threaded portion 162 may have internal threads that are arranged in a first direction (e.g. right-handed threads) and the second threaded portion 164 may have internal threads that are arranged in a second, opposite direction (e.g. left-handed threads). Accordingly, clockwise rotation of the fastener 64 will cause the first set of threads 124 to advance when engaging the first threaded portion 162, but will cause the second set of threads 126 to retract when engaging the second thread portion 164. Likewise, counter-clockwise rotation of the fastener 64 will cause the first set of threads 124 to retract when engaging the first threaded portion 162, but will cause the second set of threads 126 to advance when engaging the second threaded portion 164. In alternative embodiments, the threaded portions 162, 164 may have threads that have different pitches in the same direction, the threaded portions 162, 164 may have threads that have a different thread angle, the threaded portions 162, 164 may have threads that have different depths of threads, and the like to allow interaction with particular sets of threads 124, 126 of the fastener 64 and restrict interaction with certain other sets of threads 124, 126 of the fastener 64.

The first threaded portion 162 is positioned remote from both of the ends 156, 158 in a central portion of the insert 66. The first threaded portion 162 has a length 170 that is approximately equal to, or slightly greater than, twice the length 144 of the first set of threads 124. Accordingly, and as will be explained in further detail below, the first threaded portion 162 may accommodate two fasteners 64 during assembly of the connector assembly 28 (shown in FIG. 2). The length 170 may be longer than or shorter than twice the length 144 in alternative embodiments. For example, in one embodiment where the insert 66 accommodates a single fastener 64, the length 170 is approximately equal to, or slightly longer than, the length 144 of the first set of threads 124.

The second threaded portion 164 is positioned adjacent the first end 156 and extends into the insert 66 for a length 172. Optionally, the length 172 is approximately equal to the length 146 of the second set of threads 126, however, the length 172 may be longer than or shorter than the length 146 in alternative embodiments.

The insert 66 includes a counterbore portion 174 between the first and second threaded portions 162 and 164. The counterbore portion 174 is smooth and threadless, and allows for movement of the fastener 64 within the insert 66 along the longitudinal axis 160, as will be explained in more detail below. In the illustrated embodiment, the insert 66 also includes a third threaded portion 176 that is substantially similar to the second threaded portion 164 and a second counterbore portion 178 that is substantially similar to the counterbore portion 174. The third threaded portion 176 is positioned at the second end 158 and the second counterbore portion 178 extends between the third threaded portion 176 and the first threaded portion 162. The third threaded portion 176 and the second counterbore portion 178 are configured to receive another fastener 64 during assembly of the connector assembly 28.

Figure 6:
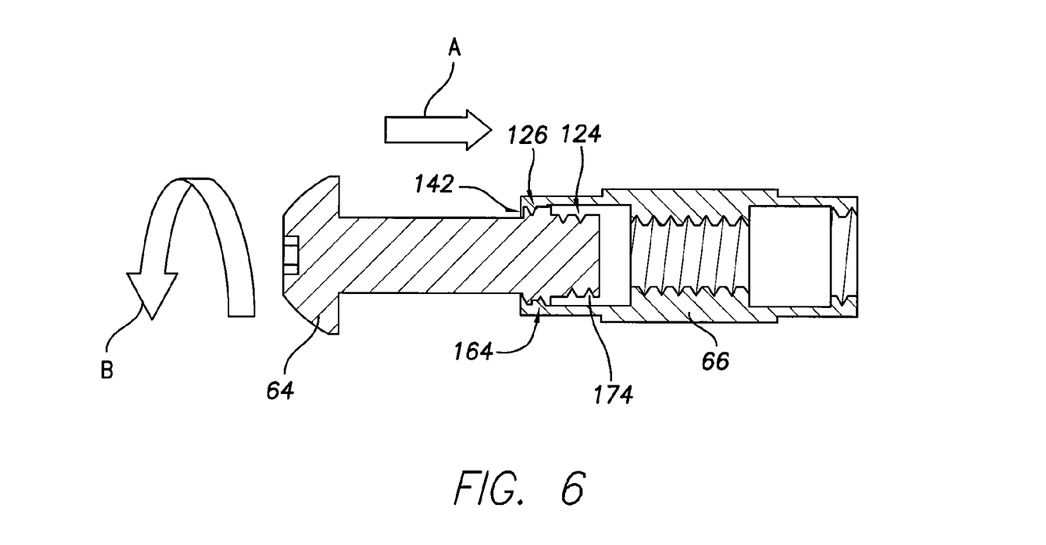
FIG. 6 illustrates an exemplary position of the fastener with respect to the threaded insert during in an initial advancement operation.

FIG. 6 illustrates an exemplary position of the fastener 64 with respect to the threaded insert 66 during in an initial advancement operation. The first set of threads 124 of the fastener 64 are initially loaded though the opening 142 of the threaded insert 66 and pass through the second threaded portion 164. Specifically, because the first diameter 148 (illustrated in FIG. 5) of the first set of threads 124 is smaller than the second diameter 168 (illustrated in FIG. 5) of the second threaded portion 164, the fastener 64 is unobstructed as the fastener 64 is loaded into the insert 66 until the second set of threads 126 engages the second threaded portion 164. When engaged, the fastener 64 is advanced with respect to the threaded insert 66, in a direction of arrow A, by rotating the fastener 64 in a counter-clockwise manner, as indicated by arrow B. Specifically, the left-handed threads of the second set of threads 126 interact with the threads of the second threaded portion 164 to advance the fastener 64 upon counter-clockwise rotation of the fastener 64. Alternatively, the second set of threads 126 and the second threaded portion 164 may have right-handed threads and may be advanced by clockwise rotation of the fastener 64. In the initial advancement operation, the fastener 64 is advanced until the second set of threads 126 are advanced beyond the second threaded portion 164. Once the second set of threads 126 are advanced beyond the second threaded portion 164 the second set of threads 126 are located within the counterbore portion 174 and are movable within the counterbore portion 174.

Figure 7:
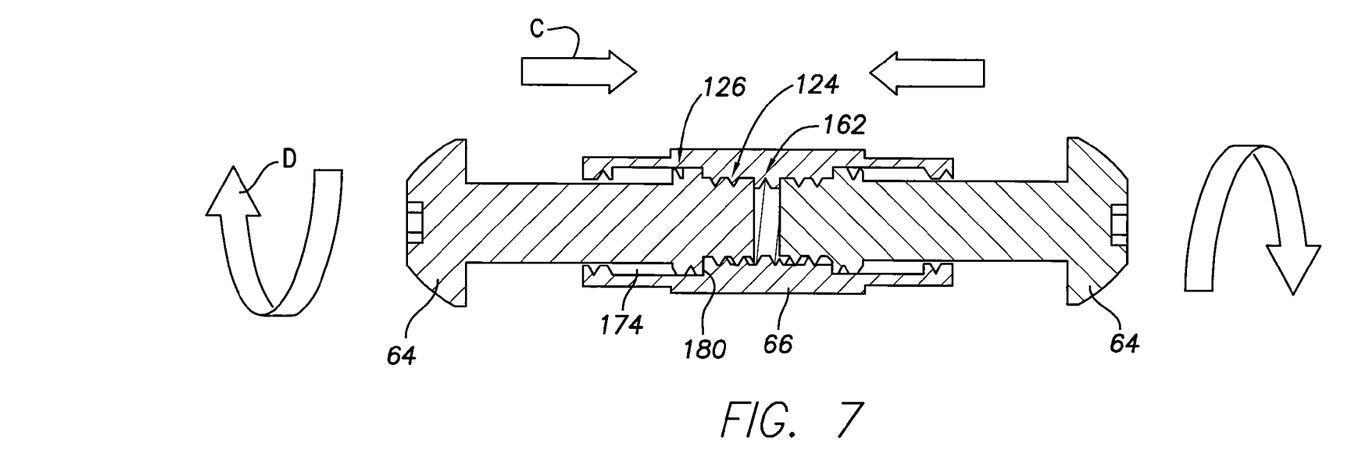
FIG. 7 illustrates exemplary positions of two fasteners with respect to the threaded insert during a final advancement operation.

FIG. 7 illustrates exemplary positions of two fasteners 64 with respect to the threaded insert 66 during a final advancement operation. As illustrated in FIG. 7, two fasteners 64 are coupled to the threaded insert 66. Both fasteners 64 are coupled in a similar manner, and the advancement operation will be described with reference to the fastener 64 on the left-hand portion of FIG. 7. In the final advancement operation, the fastener 64 is advanced within the counterbore portion 174 until the first set of threads 124 engage the first threaded portion 162. The fastener 64 is then advanced to a final advancement position with respect to the threaded insert 66, in a direction of arrow C, by rotating the fastener 64 in a clockwise manner, as indicated by arrow D. Specifically, the right-handed threads of the first set of threads 124 interact with the threads of the first threaded portion 162 to advance the fastener 64 upon clockwise rotation of the fastener 64. Alternatively, the first set of threads 124 and the first threaded portion 162 may have left-handed threads and may be advanced by counter-clockwise rotation of the fastener 64. In the final advancement operation, the fastener 64 is advanced until the side clamps 60 and 62 are properly positioned to secure the leads within the receptacles 30, 32, 34, 36, 38, 40. Optionally, a predetermined amount of clearance may be provided between the second set of threads 126 and a shoulder 180 defined between the counterbore portion 174 and the first threaded portion 162, as seen in FIG. 7. The clearance allows for full tightening of the fastener without obstruction. Optionally, a torque wrench may be used to tighten the fastener 64 and the tightening is stopped when a predetermined amount of torque is applied to the torque wrench. Tightening of the fastener 64 clockwise urges the side clamps 60, 62 (shown in FIG. 4) toward the side surfaces 76, 78 (shown in FIG. 4) of the support body 29 (shown in FIG. 4). As such, with leads inserted in the receptacles 30, 32 and 34 (shown in FIG. 3), the proximal end portions 10 (shown in FIG. 1) of the lead bodies may be securely clamped within the confronting channels 90, 92, 94, 96, 98 and 100 (shown in FIG. 4) between the side clamp 60 and support body 29; and with leads inserted in the receptacles 36, 38 and 40 (shown in FIG. 3), the proximal end portions 10 of the lead bodies may be securely clamped within the confronting channels 102, 104, 106, 108, 110 and 112 (shown in FIG. 4) between the side clamp 62 and support body 29.

Figure 8:
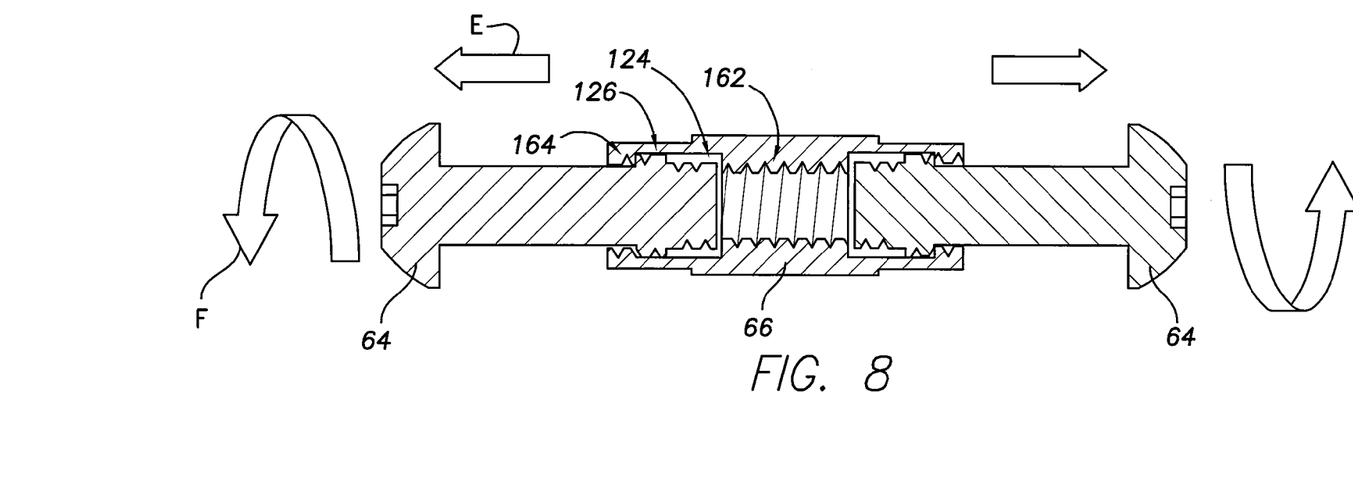
FIG. 8 illustrates exemplary positions of the two fasteners with respect to the threaded insert during an initial retraction operation.
Figure 9:
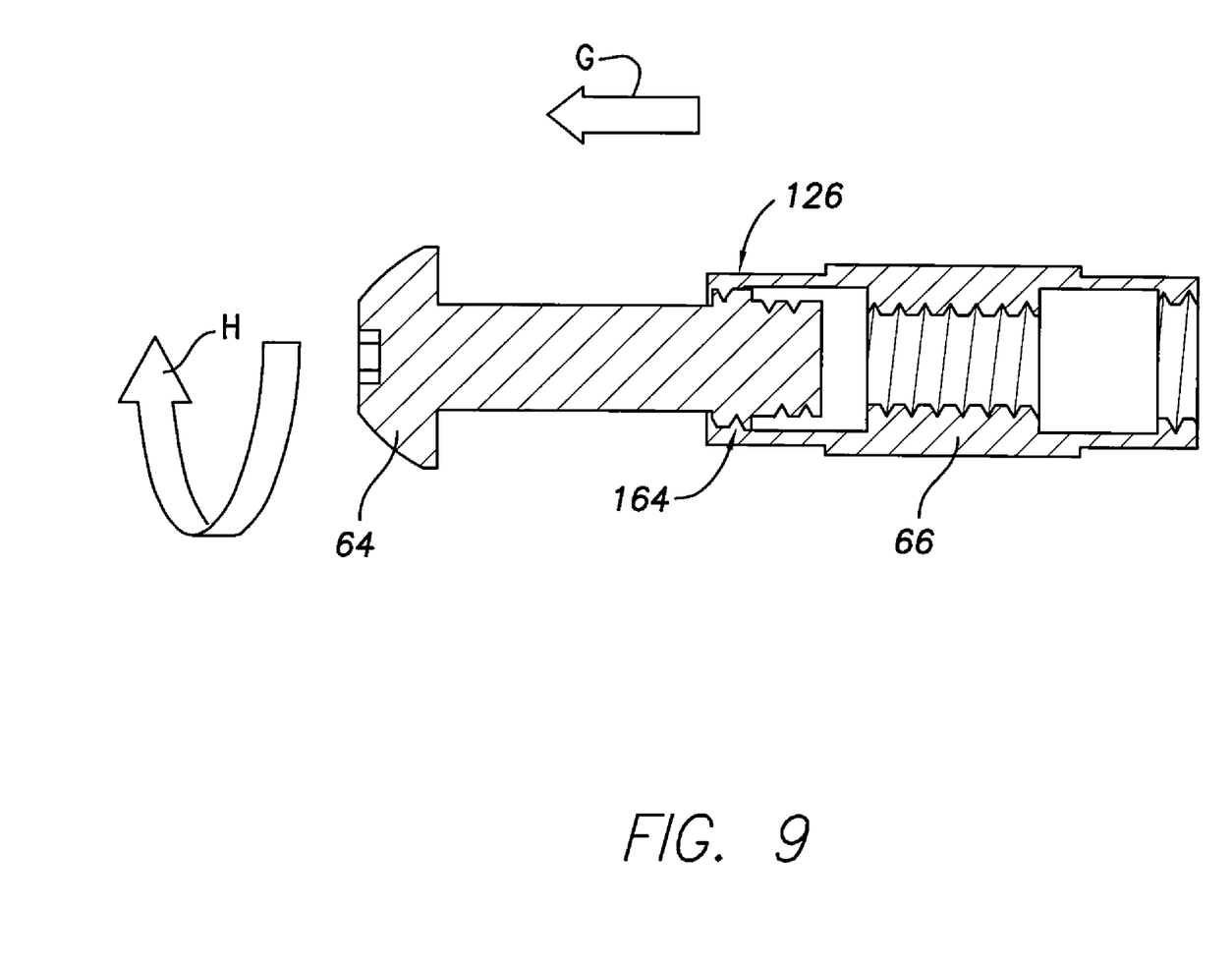
FIG. 9 illustrates an exemplary position of one of the fasteners with respect to the threaded insert during a final retraction operation.

FIG. 8 illustrates exemplary positions of two fasteners 64 with respect to the threaded insert 66 during an initial retraction operation. The retraction operation is generally the opposite of the advancement operation. Both fasteners 64 are retracted in a similar manner, and the retraction operation will be described with reference to the fastener 64 on the left-hand portion of FIG. 8. During the initial retraction operation, the first set of threads 124 are retracted from the first threaded portion 162 in a retraction direction, as indicated by arrow E, by rotating the fastener 64 in a counter-clockwise manner, as indicated by arrow F. Specifically, the right-handed threads of the first set of threads 124 interact with the threads of the first threaded portion 162 to retract the fastener 64 upon counter-clockwise rotation of the fastener 64. Once the first set of threads 124 are retracted from the first threaded portion 162, the second set of threads 126 are positioned adjacent the second threaded portion 164. Further rotation of the fastener 64 in the counter-clockwise direction, indicated by arrow F, will resist engagement of the second set of threads 126 with the second threaded portion 164, as counter-clockwise rotation causes the second set of threads 126 to advance with respect to the second threaded portion 164. Counter-clockwise rotation of the fastener 64 causes the fastener 64 to spin freely within the counterbore portion 174. As such, the second threaded portion 164 prevents removal of the fasteners 64 and the side clamps 60, 62 from the support body 29 (shown in FIG. 4) so long as a final retraction operation, as explained below with reference to FIG. 9, is not performed. When the fasteners 64 are initially retracted and in the initially retracted position, the side clamps 60, 62 (shown in FIG. 4) are loosely coupled to the support body 29 such that the leads may be removed and/or replaced, and the side clamps 60, 62 re-tightened. Accordingly, the support assembly (e.g. the support body 29, the side clamps 60, 62, and the fasteners 64) need not be completely dissembled prior to its use.

FIG. 9 illustrates an exemplary position of one of the fasteners 64 with respect to the threaded insert 66 during a final retraction operation. The final retraction operation is used to completely remove the fastener 64 from the threaded insert 66. During the final retraction operation, positive pressure is applied to the fastener 64 in the direction of retraction, indicated in FIG. 9 by arrow G. This positive pressure on the fastener 64 allows the second set of threads 126 to engage the second threaded portion 164. As such, inadvertent removal of the fastener 64 from the threaded insert 66 may be avoided unless, or until, pressure is applied to the fastener 64. The second set of threads 126 are then retracted from the second threaded portion 164 by rotating the fastener 64 in a clockwise manner, as indicated by arrow H. Specifically, the left-handed threads of the second set of threads 126 interact with the threads of the second threaded portion 164 to retract the fastener 64 upon clockwise rotation of the fastener 64. Clockwise rotation of the fastener 64 to accomplish retraction is generally counter-intuitive to a user and an unnatural operation. As such, inadvertent removal of the fastener 64 from the threaded insert 66 may be avoided by providing the second set of threads 126 and the second threaded portion 164.

While the invention has been described in terms of various specific embodiments, those skilled in the art will recognize that the invention can be practiced with modification within the spirit and scope of the claims.

What is claimed is:

1. A connector assembly for an implantable medical device, the connector assembly comprising:
   a support body having a receptacle connector extending therefrom, wherein the receptacle connector is configured to receive a portion of a lead therein, and the support body defining a fastener bore;
   a clamp having a clamp fastener bore, the clamp being movable with respect to the support body to receive the lead between the clamp and the support body; and
   a threaded fastener received in the fastener bore and the clamp fastener bore for securing the clamp to the support body, the threaded fastener having first and second sets of threads for engaging first and second threaded portions, respectively, wherein the first and second threaded portions are included in at least one of the fastener bore and the clamp fastener bore, and wherein the first and second sets of threads have different thread types; and
   an insert received in the support body, the insert defining the fastener bore and including the first and second threaded portions.

2. A connector assembly in accordance with claim 1, wherein the first threaded portion includes right-handed threads and the second threaded portion includes left-handed threads.

3. A connector assembly in accordance with claim 1, wherein the first set of threads of the threaded fastener include right-handed threads and the second set of threads of the threaded fastener includes left-handed threads.

4. A connector assembly in accordance with claim 1, wherein the threaded fastener constitutes a compound screw.

5. A connector assembly in accordance with claim 1, wherein the first set of threads have a first diameter and the second set of threads have a second diameter that is different than the first diameter.

6. A connector assembly in accordance with claim 1, wherein the threaded fastener includes a head and a shaft extending from the head to a distal end, the first set of threads extending between the distal end and the second set of threads.

7. A connector assembly in accordance with claim 1, wherein the first and second threaded portions are included within the fastener bore.

8. A connector assembly in accordance with claim 1, wherein the clamp is removable from the support body.

9. A connector assembly in accordance with claim 1, wherein the support body includes a side with a channel provided therein and with the fastener bore opening onto the side, and wherein the clamp includes a channel provided therein and positioned to align with the channel in the support body, the clamp being oriented with respect to the support body such that the channels cooperate to define at least a portion of a receptacle providing access to the receptacle connector, and the clamp being oriented with respect to the support body such that the clamp fastener bore is substantially aligned with the fastener bore.

10. A connector assembly in accordance with claim 1, wherein clockwise rotation of the threaded fastener advances the threaded fastener when the first set of threads is engaged with the first threaded portion, and clockwise rotation of the threaded fastener retracts the threaded fastener when the second set of threads is engaged with the second threaded portion; and
   wherein counter-clockwise rotation of the threaded fastener retracts the threaded fastener when the first set of threads is engaged with the first threaded portion, and counter-clockwise rotation of the threaded fastener advances the threaded fastener when the second set of threads is engaged with the second threaded portion.

11. A connector assembly in accordance with claim 1, wherein counter-clockwise rotation of the threaded fastener advances the threaded fastener when the first set of threads is engaged with the first threaded portion, and counter-clockwise rotation of the threaded fastener retracts the threaded fastener when the second set of threads is engaged with the second threaded portion; and
   wherein clockwise rotation of the threaded fastener retracts the threaded fastener when the first set of threads is engaged with the first threaded portion, and clockwise rotation of the threaded fastener advances the threaded fastener when the second set of threads is engaged with the second threaded portion.

12. A connector assembly in accordance with claim 1, further comprising:
   a second clamp having a second clamp fastener bore, the second clamp being movable with respect to the support body and configured to receive a second lead between the clamp and the support body; and
   a second threaded fastener received in the fastener bore and the second clamp fastener bore for securing the second clamp to the support body, the second threaded fastener being substantially similar to the other threaded fastener and received in the fastener bore at an opposite end as the other threaded fastener, the second threaded fastener being threadably coupled to at least one of the second clamp and the support body for securing the second clamp to the support.

13. An implantable medical system comprising:
   an implantable lead;
   a sealed casing having electronic circuitry therein;
   a header assembly for interconnecting the electronic circuitry with the implantable lead, the header assembly comprising:
   a support body having a receptacle connector extending therefrom, wherein the receptacle connector receives the implantable lead therein and is electrically coupled to the electronic circuitry, and the support body having a fastener bore;
   a clamp having a clamp fastener bore, the clamp being movable with respect to the support body to receive the lead between the clamp and the support body; and a threaded fastener received in the fastener bore and the clamp fastener bore for securing the clamp to the support body, the threaded fastener having first and second sets of threads for engaging first and second threaded portions, respectively, wherein the first and second threaded portions are included in at least one of the fastener bore and the clamp fastener bore, and wherein the first and second sets of threads have different thread types; and an insert received in the support body, the insert defining the fastener bore and including the first and second threaded portions.

14. An implantable medical device in accordance with claim 13, wherein the first threaded portion includes right-handed threads and the second threaded portion includes left-handed threads, and wherein the first set of threads of the threaded fastener include right-handed threads and the second set of threads of the threaded fastener includes left-handed threads.

15. An implantable medical device in accordance with claim 13, wherein the first and second threaded portions are included within the fastener bore.

16. An implantable medical device in accordance with claim 13, wherein the support body includes a side with a channel provided therein and with the fastener bore opening onto the side, and wherein the clamp includes a channel provided therein and positioned to align with the channel in the support body, the clamp being oriented with respect to the support body such that the channels cooperate to define at least a portion of a receptacle providing access to the receptacle connector, and the clamp being oriented with respect to the support body such that the clamp fastener bore is substantially aligned with the fastener bore.

17. An implantable medical device in accordance with claim 13, wherein clockwise rotation of the threaded fastener advances the threaded fastener when the first set of threads is engaged with the first threaded portion, and clockwise rotation of the threaded fastener retracts the threaded fastener when the second set of threads is engaged with the second threaded portion; and wherein counter-clockwise rotation of the threaded fastener retracts the threaded fastener when the first set of threads is engaged with the first threaded portion, and counter-clockwise rotation of the threaded fastener advances the threaded fastener when the second set of threads is engaged with the second threaded portion.

18. An implantable medical device in accordance with claim 13, wherein the header assembly further comprises:

a second clamp having a second clamp fastener bore, the second clamp being movable with respect to the support body and configured to receive a second lead between the clamp and the support body; and a second threaded fastener received in the fastener bore and the second clamp fastener bore for securing the second clamp to the support body, the second threaded fastener being substantially similar to the other threaded fastener and received in the fastener bore at an opposite end as the other threaded fastener, the second threaded fastener being threadably coupled to at least one of the second clamp and the support body for securing the second clamp to the support.

* * * * *